US011666551B2

(12) United States Patent
Kobayashi et al.

(10) Patent No.: US 11,666,551 B2
(45) Date of Patent: *Jun. 6, 2023

(54) AGENT FOR REDUCING AMOUNT OF AMYLOID β PROTEIN

(71) Applicant: FUJIFILM Toyama Chemical Co., Ltd., Tokyo (JP)

(72) Inventors: Hiroshi Kobayashi, Tokyo (JP); Yoshihiko Matsumoto, Tokyo (JP)

(73) Assignee: FUJIFILM Toyama Chemical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/617,607

(22) PCT Filed: Jun. 1, 2018

(86) PCT No.: PCT/JP2018/021226
§ 371 (c)(1),
(2) Date: Nov. 27, 2019

(87) PCT Pub. No.: WO2018/221732
PCT Pub. Date: Dec. 6, 2018

(65) Prior Publication Data
US 2021/0137880 A1 May 13, 2021

(30) Foreign Application Priority Data

Jun. 2, 2017 (JP) .............................. JP2017-109886
Jun. 30, 2017 (JP) .............................. JP2017-128474

(51) Int. Cl.
*A61K 31/397* (2006.01)
*A61K 9/00* (2006.01)
*A61P 25/28* (2006.01)

(52) U.S. Cl.
CPC .......... *A61K 31/397* (2013.01); *A61K 9/0053* (2013.01); *A61P 25/28* (2018.01)

(58) Field of Classification Search
CPC ...... A61K 31/397; A61K 9/0053; A61P 25/28
See application file for complete search history.

(56) References Cited

U.S. PATENT DOCUMENTS

| | | | |
|---|---|---|---|
| 6,489,481 B1 | 12/2002 | Keith et al. | |
| 7,087,594 B2 | 8/2006 | Saitoh et al. | |
| 8,119,625 B2 | 2/2012 | Iwakami et al. | |
| 10,238,632 B2 | 3/2019 | Yano | |
| 11,541,033 B2 | 1/2023 | Kobayashi et al. | |
| 11,548,878 B2 | 1/2023 | Yano et al. | |
| 2005/0070521 A1 | 3/2005 | Saitoh et al. | |
| 2005/0250843 A1 | 11/2005 | Nakada et al. | |
| 2006/0194781 A1 | 8/2006 | Saitoh et al. | |
| 2006/0205709 A1 | 9/2006 | Kimura et al. | |
| 2009/0093453 A1 | 4/2009 | Iwakami et al. | |
| 2011/0224180 A1 | 9/2011 | Pruss et al. | |
| 2012/0028953 A1 | 2/2012 | Roughley et al. | |
| 2015/0045345 A1 | 2/2015 | Inaba et al. | |
| 2015/0166472 A1 | 6/2015 | Kim et al. | |
| 2015/0203472 A1 | 7/2015 | Ceccarelli et al. | |
| 2016/0324851 A1 | 11/2016 | Friedhoff et al. | |
| 2017/0129915 A1 | 5/2017 | Tohda et al. | |
| 2017/0165227 A1 | 6/2017 | Takahashi et al. | |
| 2018/0153855 A1 | 6/2018 | Yano | |
| 2018/0369194 A1 | 12/2018 | Kano et al. | |
| 2020/0085787 A1 | 3/2020 | Kobayashi et al. | |
| 2020/0108048 A1 | 4/2020 | Kobayashi et al. | |
| 2020/0155505 A1 | 5/2020 | Kobayashi et al. | |
| 2020/0215030 A1 | 7/2020 | Kobayashi et al. | |
| 2021/0198245 A1 | 7/2021 | Yano et al. | |

FOREIGN PATENT DOCUMENTS

| | | |
|---|---|---|
| CN | 104159583 A | 11/2014 |
| EP | 3 100 725 A1 | 12/2016 |
| EP | 3 632 431 A1 | 4/2020 |
| ER | 1437353 A1 | 7/2004 |
| JP | 2002-528489 A | 9/2002 |
| JP | 2011-513374 A | 4/2011 |
| KR | 10-2008-0111131 A | 12/2008 |
| RU | 2496784 C2 | 10/2013 |
| RU | 2015112914 A | 11/2016 |
| WO | 99/11293 A1 | 3/1999 |
| WO | 03/035647 A1 | 5/2003 |

(Continued)

OTHER PUBLICATIONS

William Jagust Brain—A Journal of Neurology 2016: 139; 23-30. (Year: 2016).*
Nguyen et al Hippocampus, Jun. 2007, vol. 17, issue 6, pp. 443-455. (Year: 2007).*
Office Action dated May 26, 2020 in Indian Application No. 201947049400.
Hirata et al., "A Novel Neurotrophic Agent, T-817MA [1-{3-[2-(1-Benzothiopen-5-yl) Ethoxy] Propyl}-3-azetidinol Maleate], Attenuates Amyloid-β-Induced Neurotoxicity and Promotes Neurite Outgrowth in Rat Cultured Central Nervous System Neurons", The Journal of Pharmacology and Experimental Therapeutics, vol. 314, No. 1, pp. 252-259, 2005 (8 pages total).
Office Action dated May 29, 2020 in corresponding Russian Application No. 2019138538.

(Continued)

*Primary Examiner* — Kristin A Vajda
(74) *Attorney, Agent, or Firm* — Sughrue Mion, PLLC

(57) ABSTRACT

An object of the present invention is to provide a drug and a method which suppress progress of disease in which the amount of amyloid β protein in the brain is increased, such as Alzheimer's disease. 1-(3-(2-(1-Benzothiophen-5-yl)ethoxy)propyl)azetidin-3-ol or a salt thereof has an effect of reducing the amount of amyloid β protein in the brain parenchyma, and thus is effective as an agent for reducing the amount of amyloid β protein in the brain. Disease in which the amount of amyloid β protein in the brain is increased, such as Alzheimer's disease, can be prevented or treated by administering 1-(3-(2-(1-benzothiophen-5-yl)ethoxy)propyl)azetidin-3-ol or a salt thereof.

6 Claims, 1 Drawing Sheet

(56) References Cited

FOREIGN PATENT DOCUMENTS

| WO | 03/105830 | A1 | 12/2003 |
|---|---|---|---|
| WO | 2007/125913 | A1 | 11/2007 |
| WO | 2011/057199 | A1 | 5/2011 |
| WO | 2013/125617 | A1 | 8/2013 |
| WO | 2015/115582 | A1 | 8/2015 |
| WO | 2015/191506 | A2 | 12/2015 |
| WO | 2016/051799 | A1 | 4/2016 |
| WO | 2016/124508 | A1 | 8/2016 |
| WO | 2016/199878 | A1 | 12/2016 |
| WO | 2017/111005 | A1 | 6/2017 |

OTHER PUBLICATIONS

Uehara et al., "T-817MA, a novel neurotrophic agent, ameliorates loss of GABAergic parvalbumin-positive neurons and sensorimotor gating deficits in rats transiently exposed to MK-801 in the neonatal period", Journal of Psychiatric Research, vol. 46, No. 5, pp. 622-629, 2012 (8 pages total).

Office Action dated Jun. 10, 2021 in U.S. Appl. No. 16/617,660.

Sarva et al., "Treatment Options in Degenerative Cerebellar Ataxia: A Systematic Review", Movement Disorders Clinical Practice, 2014, vol. 1, pp. 291-298.

Horig et al., "From bench to clinic and back: Perspective on the 1st IQPC Translational Research conference", Journal of Translational Medicine, 2004, vol. 2, No. 44, pp. 1-8.

Schafer et al., "Failure is an option: learning from unsuccessful proof-of concept trials", Drug Discovery Today, 2008, vol. 13, pp. 913-916.

Decision under section 15 dated Mar. 22, 2021 issued in Indian patent application No. 201947049392.

Decision under section 15 dated Mar. 22, 2021 issued in Indian patent application No. 201947049390.

Office Action dated Jun. 1, 2021 issued in Singapore patent application No. 11201911512S, corresponding to U.S. Appl. No. 16/617,739.

Office Action dated Jun. 1, 2021 issued in Singapore patent application No. 11201911515Q.

Office Action dated Jun. 1, 2021 issued in Singapore patent application No. 11201911520U.

Office Action dated Jun. 1, 2021 issued in Singapore patent application No. 11201911519U.

Mascalchi et al., "Progression of Brain Atrophy in Spinocerebellar Ataxia Type 2: A Longitudinal Tensor-Based Morphometry Study", PLOS One, 2014, vol. 9, Issue 2, pp. 1-7, e89410.

Tosun et al., "Spatial patterns of brain amyloid-β burden and atrophy rate associations in mild cognitive impairment", Brain, 2011, vol. 134, pp. 1077-1088.

Tosun et al., "Relationship Between Regional Brain Amyloid-β Deposition and Brain Atrophy Rates in Mild Cognitive Impairment", Alzheimer's & Dementia: The Journal of the Alzheimer's Association, Jul. 1, 2010, XP027440489, vol. 6, No. 4, p. e15 (total 1 page).

Extended European Search Report dated May 7, 2020 from European Patent Office in EP Application No. 18810520.9, corresponding to U.S. Appl. No. 16/617,739.

Schneider et al., "A Phase 2 Multicenter, Randomized, Placebo-Controlled Trial to Evaluate The Efficacy and Safety of Edonerpic (T-817) In Patients with Mild to Moderate Alzheimer's Disease", Alzheimer's & Dementia: The journal of the Alzheimer's Association, Jul. 19, 2017, P4-573. vol. 13, No. 7, XP085218926, p. P1572 (total 1 page).

Yamaguchi et al., "T-817MA, a neurotrophic compound, reverses Aβ neurotoxicity and promotes neurite outgrowth through PI3-Kinase pathway in rat primary neurons", Abstract of the Annual Meeting of the Society for Neuroscience, Nov. 8, 2003, XP008135922, pp. 1-2 (total 2 pages).

Quinti et al., "A Novel Drug-Screening Platform in Microglial Cells Indentifies Potential AD Drugs", Alzheimer's & Dementia: The journal of the Alzheimer's Association, Jul. 19, 2017, XP085218817, P4-404, vol. 1, No. 13, p. P1485 (total 1 page).

Yano et al., "SIGMA-1 Receptor is a Molecular Target for Novel Neuropretectant T-817MA", Alzheimer's & Dementia: The Journal of the Alzheimer's Association, Jul. 1, 2015, XP029355158, P4-210, vol. 11, No. 7, p. P861 (total 1 page).

Nakagawa et al., "T-817MA, A Newly Developing Anti-Alzheimer's Agent, Protects Neurons And Recovers Memory Impairment in Amyloid B-Infused Rats and P301L Taumutated Mice", Alzheimer's & Dementia: The Journal of the Alzheimer's Association, Jul. 1, 2005, XP027823394, P-193, vol. 1, No. 1, p. S69-S70 (total 2 pages).

Extended European Search Report dated May 11, 2020 from European Patent Office in EP Application No. 18810759.3, corresponding to U.S. Appl. No. 16/617,584.

Office Action dated Jan. 27, 2021 issued by the Canadian Patent Office in Application No. 3,067,453, corresponding to U.S. Appl. No. 16/617,739.

Office Action dated Jan. 27, 2021 issued by the Canadian Patent Office in Application No. 3,067,455, corresponding to U.S. Appl. No. 16/617,660.

Hearing Notice dated Jan. 8, 2021 issued by the Indian Patent Office in application No. 201947049392, corresponding to U.S. Appl. No. 16/617,660.

Office Action dated Jan. 27, 2021 issued by the Canadian Patent Office in Application No. 3,067,456, corresponding to U.S. Appl. No. 16/617,552.

Hearing Notice dated Feb. 3, 2021 issued by the Indian Patent Office in Application No. 201947049400, corresponding to U.S. Appl. No. 16/617,552.

Office Action dated Jan. 29, 2021 issued by the Canadian Patent Office in Application No. 3,067,458, corresponding to U.S. Appl. No. 16/617,607 (the present application).

Hearing Notice dated Feb. 3, 2021 issued by the Indian Patent Office in Application No. 201947049390, corresponding to U.S. Appl. No. 16/617,607 (the present application).

Decision under section 15 dated Feb. 23, 2021, issued in Indian Application No. 201947049401, corresponding to U.S. Appl. No. 16/617,739.

Office Action dated Feb. 17, 2021, issued in Russian Application No. 2019138166/04, corresponding to U.S. Appl. No. 16/617,739.

Office Action dated Dec. 8, 2020, issued by the Korean Intellectual Property Office in Korean Application No. 10-2019-7035347, corresponding to U.S. Appl. No. 16/617,739.

Office Action dated Dec. 8, 2020, issued by the Korean Intellectual Property Office in Korean Application No. 10-2019-7035348, corresponding to U.S. Appl. No. 16/617,660.

Office Action dated Dec. 9, 2020, issued by the Korean Intellectual Property Office in Korean Application No. 10-2019-7035350, corresponding to U.S. Appl. No. 16/617,607 (the present application).

Office Action dated Dec. 9, 2020, issued by the Korean Intellectual Property Office in Korean Application No. 10-2019-7035349, corresponding to U.S. Appl. No. 16/617,552.

Hearing Notice dated Jan. 8, 2021, issued by the Indian Intellectual Property Office in Indian Application No. 201947049401, corresponding to U.S. Appl. No. 16/617,739.

Grimmer et al., "Beta Amyloid in Alzheimer's Disease: Increased Deposition in Brain Is Reflected in Reduced Concentration in Cerebrospinal Fluid", Biol. Psychiatry, 2009, vol. 65, No. 11, pp. 927-934 (17 pages total).

Kolobov et al., "Modern Pharmacological Models of Alzheimer's Disease", Original Articles, Experimental Neurology, 2014, vol. 8, No. 3, pp. 38-44 (32 pages total).

Office Action dated Oct. 23, 2020 in Russian Application No. 2019138538.

Office Action dated Sep. 25, 2020 in Russian Application No. 2019138166, corresponding to U.S. Appl. No. 16/617,739.

Office Action dated Apr. 27, 2020 from Russian Patent Office in Russian Application No. 2019138166/04, corresponding to U.S. Appl. No. 16/617,739.

Office Action dated Aug. 10, 2020 in Australian Application No. 2018276638, subject matter-related to U.S. Appl. No. 16/617,552.

(56) References Cited

OTHER PUBLICATIONS

Office Action dated Aug. 14, 2020 in Australian Application No. 2018277981, subject matter-related to U.S. Appl. No. 16/617,552.
Office Action dated Aug. 17, 2020 in Australian Application No. 2018277983, subject matter-related to U.S. Appl. No. 16/617,552.
Office Action dated Aug. 21, 2020 in Australian Application No. 2018277982, subject matter-related to U.S. Appl. No. 16/617,552.
Office Action dated Jul. 3, 2020 in Russian Application No. 2019138699, corresponding to U.S. Appl. No. 16/617,552.
International Search Report dated Jul. 24, 2018 in International Application No. PCT/JP2018/021225, corresponding to U.S. Appl. No. 16/617,552.
Written Opinion dated Jul. 24, 2018 in International Application No. PCT/JP2018/021225, corresponding to U.S. Appl. No. 16/617,552.
International Search Report dated Sep. 4, 2018 in International Application No. PCT/JP2018/021222, corresponding to U.S. Appl. No. 16/617,584.
Written Opinion dated Sep. 4, 2018 in International Application No. PCT/JP2018/021222, corresponding to U.S. Appl. No. 16/617,584.
International Search Report dated Jul. 24, 2018 in International Application No. PCT/JP2018/021223, corresponding to U.S. Appl. No. 16/617,739.
Written Opinion dated Jul. 24, 2018 in International Application No. PCT/JP2018/021223, corresponding to U.S. Appl. No. 16/617,739.
International Search Report dated Jul. 24, 2018 in International Application No. PCT/JP2018/021224, corresponding to U.S. Appl. No. 16/617,660.
Written Opinion dated Jul. 24, 2018 in International Application No. PCT/JP2018/021224, corresponding to U.S. Appl. No. 16/617,660.
International Search Report dated Jul. 24, 2018 in corresponding International Application No. PCT/JP2018/021226.
Written Opinion dated Jul. 24, 2018 in corresponding International Application No. PCT/JP2018/021226.
International Preliminary Report on Patentability dated Dec. 3, 2019 in International Application No. PCT/JP2018/021222, corresponding to U.S. Appl. No. 16/617,584.
International Preliminary Report on Patentability dated Dec. 3, 2019 in International Application No. PCT/JP2018/021223, corresponding to U.S. Appl. No. 16/617,739.
International Preliminary Report on Patentability dated Dec. 3, 2019 in International Application No. PCT/JP2018/021224, corresponding to U.S. Appl. No. 16/617,660.
International Preliminary Report on Patentability dated Dec. 3, 2019 in International Application No. PCT/JP2018/021225, corresponding to U.S. Appl. No. 16/617,552.
International Preliminary Report on Patentability dated Dec. 3, 2019 in corresponding International Application No. PCT/JP2018/021226.
"2012 Alzheimer's Disease Facts and Figures", Alzheimer's Association, 2012 (72 pages total) http://www.alz.org/downloads/facts_figures_2012.pdf.
Sugimoto, "Development of Anti-Alzheimer's Disease Drug Based on Beta-Amyloid Hypothesis", Yakugaku Zasshi, 2010, vol. 130, No. 4, pp. 521-526 (6 pages total).
"Epidemiological studies on Alzheimer's disease in Japan", Japanese Journal of Clinical Medicine, 2008, vol. 66 (Extra ed. 1), pp. 23-27 (5 pages total).
Press Release by Seed Planning (Dec. 28, 2010) (3 pages total); http://www.seedplanning.co.jp/press/2010/2010122801.html.
Japanese Journal of Clinical Psychopharmacology, 2011, vol. 14, No. 7, pp. 1123-1129.
Japanese Journal of Clinical Psychopharmacology, 2012, vol. 15, No. 3, pp. 311-321.
Takamura et al., "Effects of the neurotrophic agent T-817MA on oligomeric amyloid-β-induced deficits in long-term potentiation in the hippocampal CA1 subfield", Neurobiology of Aging, 2014, vol. 35, pp. 532-536 (5 pages total).
Fujifilm Corp., "II stage clinical experiment in the United States for Alzheimer's dementia therapeutic drug 'T-817MA': drastically restricting, with statistical significant difference, progress of deterioration in cognitive function with respect to patient group having this innovative two effects of reducing phosphorylation tau in cerebrospinal fluid and restricting hippocampal atrophy in brain", News release, Jul. 19, 2017 (1 page total).
Mckhann et al., "The diagnosis of dementia due to Alzheimer's disease: Recommendations from the National Institute on Aging-Alzheimer's Association workgroups on diagnostic guidelines for Alzheimer's disease", Alzheimer's Dement., May 2011, vol. 7, No. 3, pp. 263-269, (52 pages total).
Kimura et al., "T-817MA, a neurotrophic agent, ameliorates the deficits in adult neurogenesis and spatial memory in rats infused i.c.v. with amyloid-β peptide", British Journal of Pharmacology, 2009, vol. 157, pp. 451-463 (13 pages total).
Moreno et al., "Blocking effects of human tau on squid giant synapse transmission and its prevention by T-817MA", Frontiers in Synaptic Neuroscience, May 2011, vol. 3, Article 3, pp. 1-8 (8 pages total).
Fukushima et al., "T-817MA, a neuroprotective agent, attenuates the motor and cognitive impairments associated with neuronal degeneration in P301L tau transgenic mice", Biochemical and Biophysical Research Communications, 2011, vol. 407, pp. 730-734 (5 pages total).
Fukushima, "Pharmacological properties of T-817MA, a novel neurotrophic agent, for treatment of Alzheimer's disease", Folia Pharmacologica Japonica, 2010, vol. 136, pp. 11-14 (2 pages total).
Proceedings of the Annual Meeting of the Japanese Research Group on Senile Dementia, 2010, vol. 15, pp. 79-81 (3 pages total).
Lo et al., "Longitudinal Change of Biomarkers in Cognitive Decline", Archives of Neurology, 2011, vol. 68, No. 10, pp. 1257-1266 (10 pages total).
Japanese Journal of Geriatrics, 2013, vol. 50, No. 1, pp. 1-8 (8 pages total).
Jack Jr. et al., "Tracking pathophysiological processes in Alzheimer's disease: an updated hypothetical model of dynamic biomarkers", Lancet Neurology, Feb. 2013, vol. 12, No. 2, pp. 207-216 (10 pages total).
Extended European Search Report dated May 11, 2020 in European Application No. 18809579.8, corresponding to U.S. Appl. No. 16/617,552.
Extended European Search Report dated May 11, 2020 in European Application No. 18809739.8, corresponding to U.S. Appl. No. 16/617,660.
Extended European Search Report dated May 13, 2020 in European Application No. 18809110.2, corresponding to U.S. Appl. No. 16/617,607.
Office Action dated May 26, 2020 in Indian Application No. 201947049390, corresponding to U.S. Appl. No. 16/617,607.
Office Action dated May 26, 2020 in Indian Application No. 201947049392, corresponding to U.S. Appl. No. 16/617,660.
Office Action dated May 26, 2020 in Indian Application No. 201947049392, corresponding to U.S. Appl. No. 16/617,739.
Kawasaki et al., "A Neuroprotective Agent, T-817MA (1-{3-[2-(1-benzothiophen-5-yl)ethoxy]propyl}azetidin-3-ol Maleate), Prevents 1-methyl-4-phenyl-1,2,3,6-tetrahydropyridine-induced Neurotoxicity in Mice", Neuropharmacology, vol. 55, Issue 5, Oct. 2008, pp. 654-660, Abstract only.
Office Action dated Mar. 2, 2020 in Russian Application No. 2019138164, corresponding to U.S. Appl. No. 16/617,660.
Office Action dated Aug. 19, 2021 in U.S. Appl. No. 16/617,584.
Shigemori et al., "The factorial structure of the mini mental state examination (MMSE) in Japanese dementia patients", BMC Geriatrics, 2010, vol. 10, Issue 36, pp. 1-7.
Colovic et al., "Acetylcholinesterase inhibitors: Pharmacology and Toxicology", Current Neuropharmacology, 2013, vol. 11, pp. 315-335.
Communication dated Aug. 4, 2021 from the Canadian Patent Office in Canadian Application No. 3,067,456, corresponds to U.S. Appl. No. 16/617,552.
Notice of Allowance dated Sep. 28, 2021 in U.S. Appl. No. 16/617,660.
Notice of Final Rejection dated Aug. 24, 2021 from the Korean Patent Office in Korean Application No. 10-2019-7035348, corresponds to U.S. Appl. No. 16/617,660.

(56) References Cited

OTHER PUBLICATIONS

SIM integrated internal medicine understood through anatomy and pathophysiology 10 : Neurology Spinocerebellar Degeneration, May 30, 2013 (12 pages total).
Healthline, "Brain Atrophy (Cerebral Atrophy)", updated Mar. 29, 2019 https://www.healthline.com/health/brain-atrophy (10 pages total).
Office Action dated Jun. 23, 2021 in U.S. Appl. No. 16/617,739.
Office Action dated Jul. 21, 2021 in New Zealand Application No. 759585, corresponds to U.S. Appl. No. 16/617,739.
Office Action dated Jul. 21, 2021 in New Zealand Application No. 759647, corresponds to U.S. Appl. No. 16/617,660.
Office Action dated Jul. 21, 2021 in New Zealand Application No. 759657, corresponds to U.S. Appl. No. 16/617,552.
Communication dated Aug. 11, 2021 from the Canadian Patent Office in Canadian Application No. 3,067,458.
Communication dated Aug. 17, 2021 from the Mexican Patent Office in Mexican Application No. MX/a/2019/014306.
Office Action dated Jul. 22, 2021 in New Zealand Application No. 759662.
Blennow, "Cerebrospinal Fluid Protein Biomarkers for Alzheimer's Disease", The American Society for Experimental NeuroTherapeutics, Apr. 2004, vol. 1, pp. 213-225 (13 pages total).
Office Action dated Jun. 25, 2021 in Korean Application No. 10-2019-7035347, corresponding to U.S. Appl. No. 16/617,739.
Office Action dated Jul. 2, 2021 in U.S. Appl. No. 16/617,552.
Office Action dated Jun. 24, 2021 in Korean Application No. 10-2019-7035349, corresponding to U.S. Appl. No. 16/617,552.
Office Action dated Jun. 25, 2021 in Korean Application No. 10-2019-7035348, corresponding to U.S. Appl. No. 16/617,660.
Manto et al., "Animal Models of Human Cerebellar Ataxias: a Cornerstone for the Therapies of the Twenty-First Century", Cerebellum, 2009, vol. 8, pp. 137-154 (18 pages total).
Office Action dated Jul. 13, 2021 in Japanese Application No. 2019-521350, corresponding to U.S. Appl. No. 16/617,552.
Shimohama et al., Journal of Japan Senile Medicine, vol. 50, No. 1, pp. 50:1-50:8, 2013 (8 pages total).
Office Action dated Jun. 10, 2021 in Russian Application No. 2019138538, corresponding to U.S. Appl. No. 16/617,607 (the present application).
Grigorenko et al., "Molecular Basics of Alzheimer's Disease", Molekulyarnaya Biologiya, 2007, vol. 41, No. 2, pp. 331-345 (15 pages total).
Office Action dated Jun. 10, 2021 in Mexican Application No. MX/a/2019/014306, corresponding to U.S. Appl. No. 16/617,607 (the present application).
Office Action dated Jun. 24, 2021 in Korean Application No. 10-2019-7035350, corresponding to U.S. Appl. No. 16/617,607 (the present application).
Lemere et al., "Sequence of Deposition of Heterogeneous Amyloid β-Peptides and APO E in Down Syndrome: Implications for Initial Events in Amyloid Plaque Formation", Neurobiology of Disease, 1996, vol. 3, No. 1, pp. 16-32, Article No. 0003 (17 pages total).
Bae et al., "Cholesterol biosynthesis from lanosterol: molecular cloning, chromosomal localization, functional expression and liver-specific gene regulation of rat sterol $\Delta^8$-isomerase, a cholesterogenic enzyme with multiple functions", Biochem. J., 2001, vol. 353, pp. 689-699.
Berardi et al., "Novel 4-(4-Aryl)cyclohexyl-1-(2-pyridyl)piperazines as A8-A7 Sterol Isomerase (Emopamil Bonding Protein) Selective Ligands with Antiproliferative Activity", J. Med. Chem., 2008, vol. 51, No. 23, pp. 7523-7531.
Extended European Search Report dated Jul. 3, 2020, from the European Patent Office in European application No. 18873445.3, corresponds to U.S. Appl. No. 16/760,512.
Derry et al., "Mutations in a A8-A7 sterol isomerase in the tattered mouse and X-linked dominant chondrodysplasia punctata", Nature Genetics, Jul. 1999, vol. 22, pp. 286-290.
International Preliminary Report on Patentability dated May 5, 2020, issued by the International Bureau in application No. PCT/JP2018/040283.

International Search Report dated Jan. 29, 2019, issued by the International Searching Authority in application No. PCT/JP2018/040283.
Laggner et al., "Discovery of High-Affinity Ligands of sigma1 Receptor, ERG2, and Emopamil Binding Protein by Pharmacophore Modeling and Virtual Screening", J. Med. Chem., 2005, vol. 48, No. 15, pp. 4754-4764.
Moebius et al., "Identification of a 27-kDa High Affinity Phenylalkylamine-Binding Polypeptide as the sigma 1 Binding Site by Photoaffinity Labeling and Ligand-Directed Antibodies", Molecular Pharmacology, 1993, vol. 44, pp. 966-971 (8 pgs. total).
Silve et al., "Emopamil-binding Protein, a Mammalian Protein That Binds a Series of Structurally Diverse Neuroprotective Agents, Exhibits A8-A7 Sterol Isomerase Activity in Yeast", The Journal of Biological Chemistry, Sep. 13, 1996, vol. 271, No. 37, pp. 22434-22440 (8 pgs. total).
Written Opinion dated Jan. 29, 2019, issued by the International Searching Authority in application No. PCT/JP2018/040283.
Office Action dated Nov. 4, 2021 in counterpart Mexican Application No. MX/a/2019/014306.
Restriction Requirement dated Jun. 3, 2021 in U.S. Appl. No. 16/760,512.
Office Action dated Aug. 18, 2021 in U.S. Appl. No. 16/760,512.
Marquer et al., "Increasing membrane cholesterol of neurons in culture recapitulates Alzheimer's disease early phenotypes", Molecular Neurodegeneration, 2014, vol. 9, No. 60, pp. 1-13 (13 pages total).
Chemical Abstracts Registry No. 519187-30-5, Indexed in the Registry file on STN CAS Online, May 23, 2003 (1 page total).
Office Action dated Nov. 30, 2021 in Japanese Application No. 2019-521350, corresponds to U.S. Appl. No. 16/617,552.
A. Sugiyama and H. Shimada, Tau PET Imaging for Dementia in Clinical Practice, Radioisotopes, vol. 65, No. 12, pp. 517-522 (Japan Radioisotope Association, 2016).
Amano, "Neurodegenerative Diseases and Tauopathy", Shinshu Journal, 2002, vol. 50, No. 3, pp. 113-120 (8 pages total).
Y. Soeda and A. Takashima, Development of disease modifying drugs for dementia—focusing on anti-tau drugs, Clinical Neurology, vol. 54, pp. 1178-1180 (2014).
Y. Yoshiyama, Nippon Rinsho, Japanese Journal of Clinical Medicine, vol. 69, Suppl. 8, pp. 262-266 (2011).
H. Takahashi, Animal models of Alzheimer's disease for preclinical research, Folia Pharmacol. Jpn., vol. 136, No. 1, pp. 6-10(2010).
"Guidance for Industry: Estimating the Maximum Safe Starting Dose in Initial Clinical Trials for Therapeutics in Adult Healthy Volunteers", U.S. Department of Health and Human Services, Food and Drug Administration, Center for Drug Evaluation and Research (CDER), Jul. 2005 (30 pages total).
Office Action dated Dec. 8, 2021 in U.S. Appl. No. 16/760,512.
Office Action dated Dec. 15, 2021 in U.S. Appl. No. 16/617,739.
Notice of Allowance dated Dec. 15, 2021 in U.S. Appl. No. 16/617,660.
Office Action dated Dec. 7, 2021 in Mexican Application No. MX/a/2019/014300, corresponds to U.S. Appl. No. 16/617,552.
Office Action dated Dec. 20, 2021 in Korean Application No. 10-2019-7035347, corresponds to U.S. Appl. No. 16/617,739.
Chetelat et al., "Relationship between Atrophy and β-Amyloid Deposition in Alzheimer Disease", Ann Neurol, 2010, vol. 67, pp. 317-324 (8 pages total).
Office Action dated Dec. 14, 2021 in Korean Application No. 10-2019-7035349, corresponds to U.S. Appl. No. 16/617,552.
Office Action dated Dec. 14, 2021 in counterpart Korean Application No. 10-2019-7035350.
Busciglio et al., "Altered Metabolism of the Amyloid β Precursor Protein Is Associated with Mitochondrial Dysfunction in Down's Syndrome", Neuron, 2002, vol. 33, pp. 677-688 (12 pages total).
Office Action dated Jan. 28, 2022 in U.S. Appl. No. 16/617,552.
U.S. Appl. No. 16/617,584, Hiroshi Kobayashi, et al., filed Nov. 27, 2019, Pending.
U.S. Appl. No. 16/617,739, Hiroshi Kobayashi, et al., filed Nov. 27, 2019, Pending.
U.S. Appl. No. 16/617,660, Hiroshi Kobayashi, et al., filed Nov. 27, 2019, Allowed.

(56) References Cited

OTHER PUBLICATIONS

U.S. Appl. No. 16/617,552, Hiroshi Kobayashi, et al., filed Nov. 27, 2019, Pending.
U.S. Appl. No. 16/617,607 (the present application), Pending.
16/760,512, Takeaki Yano, et al., filed Apr. 30, 2020, Pending.
Aisen et al., "On the path to 2025: understanding the Alzheimer's disease continuum", Alzheimer's Research & Therapy, 2017, vol. 9, No. 60, pp. 1-10 (10 pages total).
Head et al., "Alzheimer's Disease in Down Syndrome", Eur J Neurodegener Dis., 2012, vol. 1, No. 3, pp. 353-364 (16 pages total).
Office Action dated Jan. 25, 2022 in Russian Application No. 2019138538, corresponds to U.S. Appl. No. 16/617,607.
U.S. Appl. No. 16/617,660, Hiroshi Kobayashi, et al., filed Nov. 27, 2019, Pending.
Notice of Allowance dated Mar. 14, 2022 in U.S. Appl. No. 16/617,584.
Office Action dated Feb. 18, 2022 in Canadian Application No. 3,067,456, corresponds to U.S. Appl. No. 16/617,552.
Office Action dated Mar. 2, 2022 in Mexican Application No. MX/a/2019/014302, corresponds to U.S. Appl. No. 16/617,660.
Office Action dated Mar. 3, 2022 in Mexican Application No. MX/a/2019/014310, corresponds to U.S. Appl. No. 16/617,739.
Notice of Allowance dated Apr. 1, 2022 in U.S. Appl. No. 16/617,739.
Office Action dated Mar. 1, 2022 in corresponding Mexican Application No. MX/a/2019/014306.
Office Action dated Apr. 4, 2022 in New Zealand Application No. 759662.
Office Action dated Mar. 31, 2022 in Korean Application No. 10-2019-703530.
Communication dated Apr. 12, 2022 from the Korean Patent Office in Korean Application No. 10-2019-7035347, corresponds to U.S. Appl. No. 17/617,739.
Communication dated Apr. 7, 2022 from the Korean Patent Office in Korean Application No. 10-2019-7035349, corresponds to U.S. Appl. No. 16/617,552.
Office Action dated May 6, 2022 in Chinese Application No. 201880035394.0, corresponds to U.S. Appl. No. 16/617,739.
Office Action dated May 6, 2022 in Chinese Application No. 201880035501.X, corresponds to U.S. Appl. No. 16/617,660.
Office Action dated May 6, 2022 in Chinese Application No. 201880035503.9, corresponds to U.S. Appl. No. 16/617,552.
Office Action dated May 10, 2022 in Japanese Application No. 2019-521348, corresponds to U.S. Appl. No. 16/617,739.
Office Action dated May 10, 2022 in Japanese Application No. 2019-521347, corresponds to U.S. Appl. No. 16/617,584.
Reconsideration Report by Examiner dated Apr. 28, 2022 in Japanese Application No. 2019-521350, corresponds to U.S. Appl. No. 16/617,552.
Office Action dated May 24, 2022 in Japanese Application No. 2019-521349, corresponds to U.S. Appl. No. 16/617,660.
Peng Ying et al., "Progress of clinical trials in Alzheimer's disease drugs", Acta Pharmaceutica Sinica, 2016, vol. 51, No. 8, pp. 1185-1195 (11 pages total).
Yuli Xie, Pharmaceutical and Clinical Research, 2011, vol. 19, No. 1, pp. 1-7 (7 pages total).
Buccarello et al., "Sex Impact on Tau-Aggregation and Postsynaptic Protein Levels in the P301L Mouse Model of Tauopathy" Journal of Alzheimer's Disease, 2017, vol. 56, No. 4, pp. 1279-1292 (27 pages total).
Office Action dated May 6, 2022 in corresponding Chinese Application No. 201880035521.7.
Office Action dated Jun. 6, 2022 in U.S. Appl. No. 16/617,552.
Zheng et al., "Amyloid ß Peptide induces Tau Phosphorylation and Loss of Cholinergic Neurons in Rat Primary Septal Cultures", Neuroscience, 2002, vol. 115, No. 1, pp. 201-211 (11 pages total).
Office Action dated Jun. 7, 2022 in corresponding Japanese Application No. 2019-521351.
Office Action dated Apr. 12, 2022 in Israeli Application No. 270910, corresponds to U.S. Appl. No. 16/617,660.
Office Action dated Oct. 18, 2022 by Japan Patent Office in Application No. 2019-550404, which corresponds to U.S. Appl. No. 16/760,512.
Office Action dated Aug. 15, 2022 in U.S. Appl. No. 16/617,739.
Notice of Allowance dated Aug. 15, 2022 in U.S. Appl. No. 16/617,584.
Office Action dated Jun. 26, 2022 in Israeli Application No. 270912, corresponds to U.S. Appl. No. 16/617,552.
Hanney et al., "Memantine for dementia in adults older than 40 years with Down's syndrome (Meadows): a randomised, double-blind, placebo-controlled trial", Lancet, 2012, vol. 379, pp. 528-536 (9 pages total).
Livingstone et al., "Pharmacological interventions for cognitive decline in people with Down syndrome (Review)", Cochrane Database of Systematic Review, 2015, Issue 10, (57 pages total).
Office Action dated Nov. 8, 2022 in Japanese Application No. 2019-521351, corresponds to U.S. Appl. No. 16/617,607.
Kimihiro Kimura et al., T-817MA ameliorates cognitive impairment in the Tg2576 transgenic mouse, Society for Neuroscience, Nov. 12-16, 2016.
Office Action dated Nov. 15, 2022 in Japanese Application No. 2019-521347, corresponds to U.S. Appl. No. 16/617,584.
Office Action dated Nov. 15, 2022 in Japanese Application No. 2019-521348, corresponds to U.S. Appl. No. 16/617,739.
Office Action dated Jul. 26, 2022 in Brazilian Application No. BR1120190249834, corresponds to U.S. Appl. No. 16/617,607.
Office Action dated Aug. 29, 2022 in Korean Application No. 10-2022-7022765, corresponds to U.S. Appl. No. 16/617,552.
Office Action dated Aug. 29, 2022 in Korean Application No. 10-2022-7022766, corresponds to U.S. Appl. No. 16/617,552.
Office Action dated Sep. 13, 2022 in Brazilian Application No. BR1120190248510, corresponds to U.S. Appl. No. 16/617,739.
Office Action dated Sep. 13, 2022 in Brazilian Application No. BR1120190248811, corresponds to U.S. Appl. No. 16/617,660.
Office Action dated Jun. 27, 2022 in Israeli Application No. 270922, corresponds to U.S. Appl. No. 16/617,739.
Decision of Refusal dated Jan. 18, 2023 issued in the related Chinese patent application No. 201880035394.0, corresponds to U.S. Appl. No. 16/617,739.
Duygu Tosun, et al., "Spatial patterns of brain amyloid-β burden and atrophy rate associations in mild cognitive impairment", Brain A Journal of Neurology, 2011, vol. 134, pp. 1077-1088.
Mario Mascalchi, et al., "Progression of Brain Atrophy in Spinocerebellar Ataxia Type 2: A Longitudinal Tensor-Based Morphometry Study", PLOS One, Feb. 2014, vol. 9, Issue 2, e89410, 7 pages.
Masaya Nakagawa, et al., "T-817MA, A Newly Developing Anti-Alzheimer's Agent, Protects Neurons and Recovers Memory Impairment In Amyloid B-Infused Rats and P301L Tau-Mutated Mice", Abstracts: Pharmacological Treatments, 1 (Suppl 1), 2005, pp. S69-S70.
Office Action dated Jan. 18, 2023 issued in the related Chinese patent application No. 201880035503.9, corresponds to U.S. Appl. No. 16/617,552.
Office Action dated Jan. 5, 2023 issued in the related Singapore patent application No. 11201911515Q, corresponds to U.S. Appl. No. 16/617,660.
Office Action dated Jan. 5, 2023 issued in the Singapore patent application No. 11201911512S, corresponds to U.S. Appl. No. 16/617,739.
Office Action dated Jan. 5, 2023 issued in the related Singapore patent application No. 11201911520U, corresponds to U.S. Appl. No. 16/617,552.
Preeti J. Khandelwal, et al., "Wild type and P301L mutant Tau promote neuro-inflammation and α-Synuclein accumulation in lentiviral gene delivery modles", Mol Cell Neurosci, Jan. 2012, vol. 49, No. 1; pp. 44-53 (22 pages).
W.-H. Zheng, et al., "Amyloid β Peptide Induces Tau Phosphorylation and Loss of Cholinergic Neurons In Rat Primary Septal Cultures", Neuroscience, 2002, vol. 115, No. 1, pp. 201-211.
Notice of Allowance dated Dec. 7, 2022 in U.S. Appl. No. 16/617,739.
Office Action dated Jan. 10, 2023 in U.S. Appl. No. 16/617,552.
Ramesh J. L. Kandimalla, et al., "CSF p-Tau levels in the prediction of Alzheimer's disease", Biology Open 2, 2013, pp. 1119-1124.

(56) References Cited

OTHER PUBLICATIONS

Herman Moreno, et al., "Blocking effects of human tau on squid giant synapse transmission and its prevention by T-817 MA", Frontiers in Synaptic Neuroscience, 2011, vol. 3, Article 3, 8 pages.
Ni-Chung Lee, et al., "Blood Beta-Amyloid and Tau in Down Syndrome: A Comparison with Alzheimer's Disease", Frontiers in Aging Neuroscience, Jan. 17, 2017, vol. 8, Article 316 (8 pages).
Official Action dated Jan. 18, 2023 issued in corresponding Chinese patent application No. 201880035521.7.
Official Action dated Jan. 5, 2023 issued in corresponding Singapore patent application No. 11201911519U.
Tatsuo Kimura, et al., "T-817MA, a neurotrophic agent, ameliorates the deficits in adult neurogensis and spatial memory in rats infused i.c.v. with amyloid-β peptide", British Journal of Pharmacology, 2009, vol. 157, pp. 451-463.
Tetsuo Fukushima, "New regulation neurotrophic factor-like low molecular weight compound T817MA", 2010, 2 pages.
Tetsuo Fukushima, et al., "T-817MA, a neuroprotective agent, attenuates the motor and cognitive impairments associated with neuronal degeneration in P301L tau transgenic mice", Biochemical and Biophysical Research Communications, 2011, vol. 407, pp. 730-734.
Yusaku Takamura, et al., "Effects of the neurotrophic agent T-817MA on oligomeric amyloid-β-induced deficits in long-term potentiation in the hippocampal CA1 subfield", Neurobiology of Aging, 2014, vol. 35, pp. 532-536.
Folia Pharmacologica Japonica, 2010, vol. 136, pp. 11-14 (5 pages).
Mikio Shoji "Biomarker of Dementia: Contribution [to Diagnosis and Prediction]", Animus, 2014, No. 81, pp. 17-26 (10 pages).
Official Action dated Mar. 7, 2023 issued in Japanese patent application No. 2022-028810, corresponding to U.S. Appl. No. 16/617,552.
Office Action dated Mar. 27, 2023 in Korean Patent Application No. 10-2022-7022765, corresponding to U.S. Appl. No. 16/617,552.
Office Action dated Mar. 27, 2023 in Korean Patent Application No. 10-2022-7022766, corresponding to U.S. Appl. No. 16/617,552.
"History of Changes for Study: NCT02079909: Efficacy and Safety of T-817MA in Patients with Mild to Moderate Alzheimer's Disease (US202)", ClinicalTrials.gov.archive, U.S. National Library of Medicine, May 16, 2017 (13 pages).

* cited by examiner

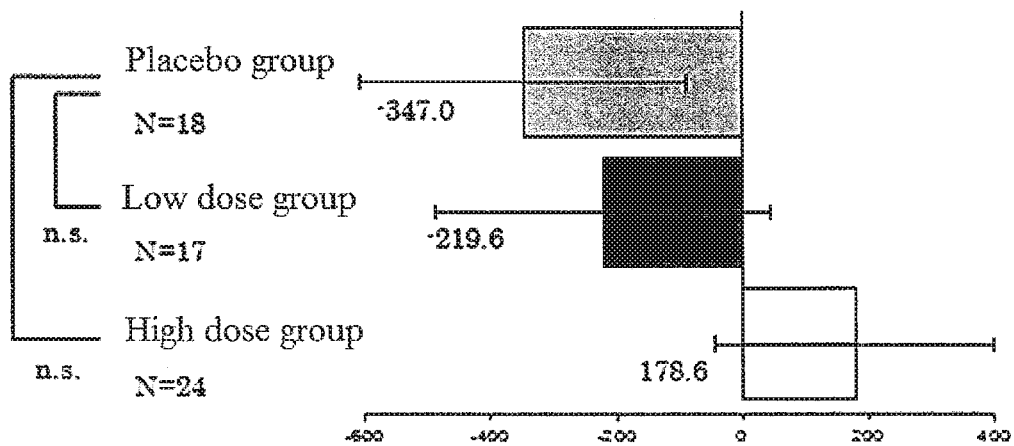
change in the concentration of Aβ-38 in cerebrospinal fluid (pg/mL)
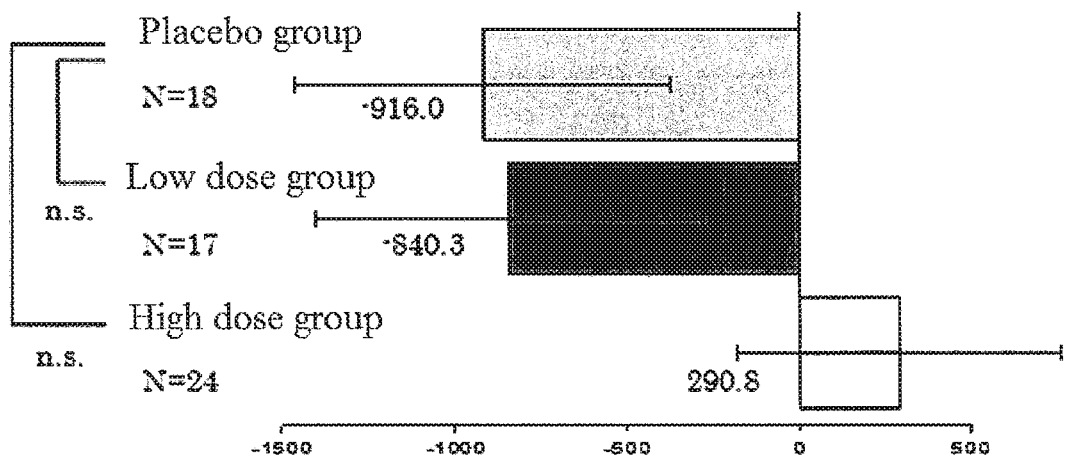
change in the concentration of Aβ-40 in cerebrospinal fluid (pg/mL)
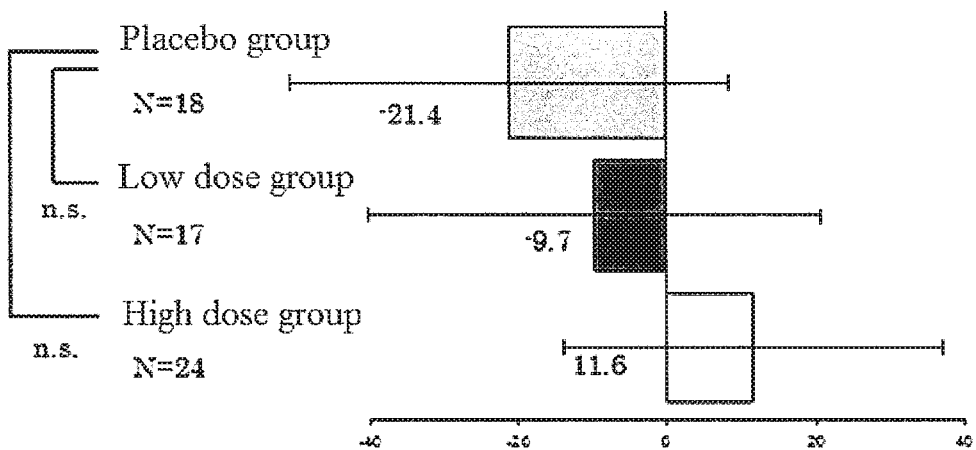
change in the concentration of Aβ-42 in cerebrospinal fluid (pg/mL)

AGENT FOR REDUCING AMOUNT OF AMYLOID β PROTEIN

CROSS REFERENCE TO RELATED APPLICATIONS

This application is a National Stage of Application No. PCT/JP2018/021226 filed Jun. 1, 2018, claiming priority based on Japanese Patent Application No. 2017-109886 filed Jun. 2, 2017 and Japanese Patent Application No. 2017-128474 filed Jun. 30, 2017.

TECHNICAL FIELD

The present invention relates to an agent for reducing the amount of amyloid β protein, comprising 1-(3-(2-(1-benzothiophen-5-yl)ethoxy)propyl)azetidin-3-ol or a salt thereof as an active ingredient.

BACKGROUND ART

Dementia is a neurodegenerative disease with significantly reduced cognitive function caused by, for example, brain atrophy and/or cerebrovascular disorder. Dementia is classified into some types by its cause, and 60% to 80% of the patients with dementia suffers from Alzheimer's disease (AD) (Non Patent Literature 1). The pathogenesis of AD is complicated, and the cause is considered to be the formation of senile plaques due to coagulation of amyloid-β protein (Aβ) or neurofibrillary changes caused by coagulation of phosphorylated Tau protein (p-Tau) (Non Patent Literature 2). The number of patients with AD in Japan is estimated to be about more than 1,160,000. The incidence is higher in advanced age, and thus with the aging of society, the number of patients is expected to increase rapidly, causing a greater burden on patients' family and a sharp rise in medical and nursing care expenses in the future (Non Patent Literatures 3, 4). Thus, treatment of AD is important for not only preventing patients' quality of life from decreasing and reducing burden on their family thereafter, but also reducing medical expenses in the future aging society.

Symptoms of dementia include core symptoms of cognitive impairment and peripheral symptoms such as problem behaviors seen when patients with cognitive impairment interact with people around them (Non Patent Literature 5). At present four agents are used as an agent for treating AD in Japan: donepezil hydrochloride, galantamine hydrobromide, and rivastigmine, which are acetylcholinesterase inhibitors, and memantine hydrochloride which is a N-methyl-D-aspartate receptor antagonist. These are all capable of reducing core symptoms or peripheral symptoms. However, these drugs are symptomatic drugs which improve core symptoms or peripheral symptoms for a certain period of time, and do not suppress neurodegeneration in AD. Although these drugs are temporally effective in improving cognitive function at the beginning of use, the cognitive function usually becomes worse than cognitive function before the treatment, after about 48 weeks or more (Non Patent Literature 6).

The amount of Aβ, which is considered to cause the development of AD, is known to be controlled by its production by cleavage of precursor protein and its removal by glial cells in the brain. Aβ is known to accumulate in the brain with age as a soluble oligomer or insoluble aggregate. Soluble Aβ in the brain is incorporated into astrocytes and microglia. On the other hand, Aβ which has become insoluble and been aggregated is phagocytosed by microglia expressing complement receptor and IgG receptor, and excreted into cerebrospinal fluid (CSF), lymph or blood (Non-patent Literature 7). The amount of Aβ in CSF is decreased with the progress of AD (Non-patent Literature 8). This is thought to suggest an increased amount of aggregated Aβ in the brain. A literature on diagnostic criteria of AD describes a reduced amount of Aβ in CSF and an increased accumulation of amyloid tracer in PET imaging as a biomarker of deposition of Aβ in the brain (Non-patent Literature 9).

1-(3-(2-(1-benzothiophen-5-yl)ethoxy)propyl)azetidin-3-ol (hereinafter referred to as "Compound A") or a salt thereof is known to have neuroprotective, nerve regeneration-promoting and neurite outgrowth actions, and be useful as a therapeutic agent for central and peripheral neurological diseases (Patent Literature 1). Furthermore, a publication discloses that usually the drug may be administered to an adult in a dose or divided doses of 0.01 to 500 mg per day (Patent Literature 2).

PRIOR ART LITERATURES

Patent Literature

Patent Literature 1: International Publication No. WO 2003/035647
Patent Literature 2: International Publication No. WO 2003/105830

Non-Patent Literature

Non Patent Literature 1: 2012 Alzheimer's Disease Facts and Figures. (http://www.alz.org/downloads/facts_figures_2012.pdf)
Non Patent Literature 2: YAKUGAKU ZASSHI, 2010, Vol. 130, No. 4, pp. 521-526
Non Patent Literature 3: Japanese Journal of Clinical Medicine, 2008, Vol. 66 (Extra ed. 1), pp. 23-27
Non Patent Literature 4: Press Release by Seed Planning (Dec. 28, 2010) (http://www.seedplanning.co.jp/press/2010/2010122801.html)
Non Patent Literature 5: Japanese Journal of Clinical Psychopharmacology, 2011, Vol. 14, No. 7, pp. 1123-1129
Non Patent Literature 6: Japanese Journal of Clinical Psychopharmacology, 2012, Vol. 15, No. 3, pp. 311-321
Non-patent Literature 7: Proceedings of the Annual. Meeting of the Japanese Research Group on Senile Dementia, 2010, Vol. 15, pp. 79-81
Non-patent Literature 8: Archives of Neurology, 2011, Vol. 68, No. 10, pp. 1257-1266
Non-patent Literature 9: Japanese Journal of Geriatrics, 2013, Vol. 50, No. 1, pp. 1-8

SUMMARY OF INVENTION

Problem to be Solved by the Invention

Drugs which suppress progress of AD by inhibiting neurodegeneration need to be developed early. An object of the present invention is to provide a drug and a method which suppress progress of disease in which the amount of Aβ in the brain is increased, such as AD.

Means for Solving Problem

In such circumstances, the present inventors have found that Compound A or a salt thereof has an effect of increasing the amount of Aβ in CSF, in other word, an effect of reducing the amount of Aβ in the brain parenchyma, and the present invention has been completed.

The present invention provides the following.

(1) An agent for reducing the amount of Aβ in the brain, comprising Compound A or a salt thereof as an active ingredient.

(2) The agent for reducing the amount of Aβ according to (1), wherein the amount of Aβ in the brain is reduced by increasing the amount of Aβ in CSF.

(3) The agent for reducing the amount of Aβ according to (1) or (2), wherein the agent is orally administered in a dose of 100 mg to 400 mg in Willis of Compound A once a day.

(4) The agent for reducing the amount of Aβ according to (1) or (2), wherein the agent is orally administered in a dose of 160 mg or 320 mg in terms of Compound A once a day.

(5) The agent for reducing the amount of Aβ according to any one of (1) to (4), wherein the agent is for administration to a patient with a disease in which the amount of Aβ in the brain is increased.

(6) The agent for reducing the amount of Aβ according to any one of (1) to (4), wherein the agent is for administration to a patient with AD, Probable AD, Possible AD, Preclinical AD, Prodromal AD, mild cognitive impairment due to AD (MCI due to ADI) or MCI.

(7) The agent for reducing the amount of Aβ according to any one of (1) to (4), wherein the agent is for administration to a patient with AD, MCI due to AD or MCI.

The present invention also provides the following.

(a) An agent for increasing the amount of Aβ in CSF, comprising Compound A or a salt thereof as an active ingredient.

(b) Compound A or a salt thereof for use in a therapeutic measure for reducing the amount of Aβ in the brain.

(c) Compound A or a salt thereof for use in a therapeutic measure for increasing the amount of Aβ in CSF.

(d) A method of reducing the amount of Aβ in the brain, comprising administering Compound A or a salt thereof to a patient.

(e) A method of increasing the amount of Aβ in CSF, comprising administering Compound A or a salt thereof to a patient.

(f) Use of Compound A or a salt thereof for producing an agent for reducing the amount of Aβ in the brain.

(g) Use of Compound A or a salt thereof for producing an agent for increasing the amount of Aβ in CSF.

Advantageous Effects of Invention

The amount of Aβ in CSF can be increased and the amount of Aβ in the brain parenchyma can be reduced by administering Compound A or a salt thereof, and thus a disease in which the amount of Aβ in the brain is increased, such as AD, can be prevented or treated.

BRIEF DESCRIPTION OF DRAWINGS

FIG. 1 is a graph showing change in the concentration of Aβ (Aβ-38, Aβ-40 and Aβ-42) in cerebrospinal fluid at week 52 from the baseline. "n.s." means that there was no statistically significant difference.

EMBODIMENTS FOR CARRYING OUT THE INVENTION

Hereinafter the present invention will be described in detail.

In the present description, the respective terms have the following meaning unless otherwise specified.

In the present description, the numerical range shown with "to" represents a range inclusive of the value before and after "to" as the minimum and maximum value, respectively.

Compound A means 1-(3-(2-(1-benzothiophen-5-yl)ethoxy)propyl)azetidin-3-ol.

Examples of salts of Compound A include known salts of a basic group such as amino group or an acidic group such as hydroxyl group or carboxyl group.

Examples of salts of a basic group include salts with a mineral acid such as hydrochloric acid, hydrogen bromide, nitric acid and sulfuric acid; salts with an organic carboxylic acid such as formic acid, acetic acid, citric acid, oxalic acid, fumaric acid, maleic acid, succinic acid, malic acid, tartaric acid, aspartic acid, trichloroacetic acid and trifluoroacetic acid; mid salts with a sulfonic acid such as methanesulfonic acid, benzenesulfonic acid, p-toluenesulfonic acid, mesitylenesulfonic acid and naphthalenesulfonic acid.

Examples of salts of an acidic group include salts with an alkali metal such as sodium and potassium; salts with an alkaline earth metal such as calcium and magnesium; ammonium salts; and salts with a nitrogen-containing organic base such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-efenamin and N,N-dibenzylethylenediamine.

Of the above salts, pharmacologically acceptable salts are preferred, and salts with maleic acid are more preferred.

In the case where Compound A or a salt thereof has isomers (e.g., optical isomers, geometric isomers and tautomers), the present invention includes all these isomers and also includes hydrates, solvates and any crystal forms thereof.

Examples of diseases in which the amount of Aβ in the brain is increased include AD, Probable AD, Possible AD, Preclinical AD, Prodromal AD, MCI due to AD, MCI and Down syndrome.

In an embodiment of the invention, examples preferably include AD, Probable AD, Possible AD, Preclinical AD, Prodromal AD, MCI due to AD and MCI, more preferably AD, MCI due to AD and MCI, and further preferably AD and MCI due to AD.

Diagnosis of AD is described in Alzheimer's Dement., May 2011, Vol. 7, No. 3, pp. 263-292.

Prevention means to prevent the onset of a specific disease or at least one symptom caused by the disease.

Treatment means to reduce or improve at least one symptom caused by a specific disease with which a subject is affected, and delay the progress of the disease.

In an embodiment of the present invention, prevention means to inhibit or delay the onset or progress of increase in the amount of insoluble Aβ in the brain in a patient with, for example, AD. Treatment means to inhibit or delay the progress of increase in the amount of insoluble Aβ in the brain or to reduce the amount of insoluble Aβ in the brain.

Mild to moderate Alzheimer's disease may be clinically diagnosed as "probable AD" according to the diagnosis criteria provided by the National Institute of Neurological and Communicative Disorders and Stroke/the Alzheimer's Disease and Related Disorders Associations (NINCDS-ADRDA).

A usual doctor may reasonably make clinical diagnosis of "mild to moderate Alzheimer's disease" using standard criteria. For example, according to the score of the standardized Mini-Mental State Examination (MMSE, scores of 0 to 30), clinical diagnosis of mild to moderate, moderate, or moderate to severe AD is provided. The MMSE (Folstein, Folstein and McHugh, 1975) is a simple test of cognitive function including an interview with patients. Orientation, memory, calculation and attention, language skills and other functions are assessed. The total score is 30. The lower the score, the higher the level of impairment of cognitive function.

In Test Examples of the present invention, patients with an MMSE score of 12 to 22 at the start of the test (screening) were determined as mild to moderate AD. Note that the MMSE is not the only way to clinically determine the grade of AD, though convenient.

The relationship between cerebrospinal fluid (CSF) biomarkers and conditions of AD is widely studied. Amyloid Aβ protein (Aβ-38, Aβ-40 and Aβ-42) in CSF may reflect the level of deposition of amyloid in the brain. Change in Aβ may indicate the effect of a drug for metabolism, deposition or elimination of A.

Compound A or a salt thereof used in the present invention may be prepared by a method known per se or by combining such methods, or by the method disclosed in Patent Literature 1.

Compound A or a salt thereof used in the present invention may be blended with various pharmaceutical additives such as an excipient, a binding agent, a disintegrating agent, a disintegration inhibitor, a consolidation/adhesion-preventing agent, a lubricant, an absorption/adsorption carrier, a solvent, a bulking agent, an isotonic agent, a solubilizer, an emulsifier, a suspending agent, a thickener, a coating agent, an absorption enhancer, a gelling/procoagulant agent, a light stabilizer, a preservative, a desiccant, an emulsification/suspension/dispersion stabilizer, a color protecting agent, a deoxidant/antioxidant, a flavoring agent, a coloring agent, a foaming agent, an antifoaming agent, a soothing agent, an antistatic agent, a buffer, and/or a pH adjuster to give a pharmaceutical preparation such as an oral preparation (e.g., tablets, capsules, powders, granules, fine granules, pills, suspensions, emulsions, liquids, and syrups), injections, eye drops, nasal sprays and transdermal agents. Tablets are preferred as an oral dosage form for patients with AD.

The above agents are formulated by a usual method.

The method of administration of Compound A, which is not particularly limited, is accordingly determined based on the form of the preparation, the age, sex and other conditions of the patient and the level of symptoms of the patient.

The dose of Compound A is accordingly selected based on the administration, the age, sex, type of disease and other conditions of the patient.

The agent may be administered to an adult in a dose or divided doses of usually 40 to 500 mg in terms of Compound A per day. The agent is administered in a dose or divided doses of preferably 100 to 400 mg in terms of Compound A per day, and administered in a dose of further preferably 160 mg or 320 mg in terms of Compound A per day.

In the administration of Compound A or a salt thereof in the present invention, prevention or treatment by administration of acetylcholinesterase inhibitors (AChEIs) may also be included. Examples of AchEIs include donepezil hydrochloride, galantamine hydrochloride, rivastigmine tartrate and tacrine hydrochloride.

In the present invention, the subject may have undergone prevention or treatment by administration of AChEI for at least 6 months before administration of Compound A or a salt thereof.

Next, the present invention will be described with reference to Test Examples and Preparation Examples, but the present invention is not limited thereto.

Maleate of Compound A was used as the test compound.

Test Example 1 Multicenter randomized double-blind phase II placebo-controlled trial for assessing effectiveness and safety of Compound A in mild to moderate AD patients Subject (selection criteria): Patients were screened in a period from 42 days before treatment assignment to the assignment based on the following selection criteria.

Patients who were probable AD and are 55 years old or older and 85 years old or younger at the time of obtaining consent of screening.

Patients with an MMSE score of 12 to 22 at the time of screening

Patients with a Modified Hachinski Ischemia Scale score of 4 or less

Patients who have been treated with a donepezil hydrochloride or rivastigmine transdermal system for at least 4 months before the baseline and with a stable dose thereof for 3 months before the baseline.

In the case of patients who have received memantine in addition to being treated with a donepezil hydrochloride or rivastigmine transdermal system, patients who have been treated with memantine for at least 4 months before the baseline and with a stable dose thereof for 3 months before the baseline.

Patients whose brain MRI or CT results match AD at the time of screening

Organization of groups: Patients matched (484 patients) were randomly divided into the following 3 groups and the trial was started.

(1) High dose group: 224 mg of a test compound (160 mg in terms of Compound A) was orally administered once a day for 4 weeks and then 448 mg of a test compound (320 mg in terms of Compound A) was orally administered once a day for 48 weeks (158 patients)

(2) Low dose group: 224 mg of a test compound (160 mg in terms of Compound A) was orally administered once a day for 52 weeks (166 patients)

(3) Placebo group: placebo was orally administered once a day for 52 weeks (158 patients) Method of assessment:

Cerebrospinal Fluid Biomarker

Cerebrospinal fluid was collected by lumber puncture from subjects at baseline (within 2 weeks before the first day of administration of investigational drug) and after 52 weeks (within 2 weeks before week 52), and divided into 9-ml aliquots in polyethylene tubes and stored at −80° C. The AP-42 value in the cerebrospinal fluid was measured by sandwich ELIZA which has been designed for measurement of Aβ including 1 amino acid and 42 amino acids.

Statistical Analysis:

Change in cerebrospinal fluid (CSF) biomarkers at week 52 from the baseline was compared by analysis of covariance between a high dose group and a placebo group, and between a low dose group and the placebo group. For models, the baseline of cerebrospinal fluid (CSF) biomarkers was included as a covariate and the significance level was 5%.

Results: Shown Below

Change in the concentration of cerebrospinal fluid (CSF) biomarkers (Aβ-38, Aβ-40, Aβ-42) at week 52 from the baseline is shown in Table 1 and FIG. 1.

TABLE 1

| Group | Number of cases/ statistics | Biomarker | | |
|---|---|---|---|---|
| | | Aβ-38 (pg/mL) | Aβ-40 (pg/mL) | Aβ-42 (pg/mL) |
| High dose group | Number of cases | 24 | 24 | 24 |
| | Least square means (standard error) | 178.64 (221.978) | 290.84 (466.956) | 11.55 (25.578) |
| | Difference from placebo group (95% Confidence interval) | 525.66 (−157.19, 1208.50) | 1206.87 (−236.41, 2650.16) | 32.90 (−45.62, 111.41) |
| | p-value | 0.1286 | 0.0995 | 0.4047 |
| Low dose group | Number of cases | 17 | 17 | 17 |
| | Least square means (standard error) | −219.58 (266.774) | −840.32 (559.467) | −9.70 (30.362) |
| | Difference from placebo group (95% Confidence interval) | 127.43 (−625.01, 879.87) | 75.71 (−1507.58, 1659.00) | 11.65 (−73.37, 96.67) |
| | p-value | 0.7356 | 0.9240 | 0.7847 |
| Placebo group | Number of cases | 18 | 18 | 18 |
| | Least square means (standard error) | −347.01 (258.755) | −916.03 (546.085) | −21.35 (29.584) |

For the change in the concentration of Aβ in the cerebrospinal fluid at week 52 from the baseline, the concentration of Aβ tended to be increased in a dose dependent manner in the Compound A group compared to the placebo group.

Preparation Example 1

0.9726 g of magnesium stearate (magnesium stearate, Merck) was added to 174.03 g of maleate of Compound A and the mixture was mixed for 30 minutes. The mixed powder was compression-molded by a roller compactor (TF-LABO (roll pressure 3 MPa), Freund Corporation), and the solid obtained by molding was granulated. 49.51 g of lactose (FlowLac 90, Meggle Japan), 16.50 g of crystalline cellulose (CEOLUS PH302, Asahi Kasei Chemicals) and 6.67 g of croscarmellose sodium (Primellose, DMV Japan) were each sieved through a sieve with an opening of 850 μm and added to 60.0 g of the resulting granulated powder, and the mixture was mixed for 10 minutes. 0.6667 g of magnesium stearate was added to the mixed powder and the mixture was mixed for 30 minutes. The mixed powder was tableted by a tableting machine (HT-P18A, Hata Tekkosho) at a tableting pressure of about 12 kN using a pestle having a double rounded surface with a tablet diameter of 8.5 mm to obtain round uncoated tablets each weighing 250 mg. The uncoated tablets were coated with 8 mg of a coating agent per tablet using a film coater DRC-200 (Powrex), and then a small amount of carnauba wax (Polishing Wax-105, Nippon Wax) was added thereto to give film-coated tablets.

Preparation Example 2

60.90 g of mannitol (Parteck M200, Merck) and 3.60 g croscarmellose sodium were added to 53.70 g of maleate of Compound A and the mixture was mixed for 10 minutes. L80 g of magnesium stearate was added to the mixed powder and the mixture was mixed for 30 minutes. The mixed powder was tableted at a tableting pressure of about 10 kN using a pestle having a double rounded surface with a tablet diameter of 8.5 mm to obtain round uncoated tablets each weighing 250 mg. The uncoated tablets were coated with 8 mg of a coating agent (Opadry 03F44057, 00F440000 (hypromellose 2910: 71.5%, Macrogol 6000: 14.166%, talc: 7.167%, titanium oxide: 7.067%©, iron sesquioxide: 0.1%), Colorcon Japan LLC) per tablet, and then a small amount of carnauba wax was added thereto to give film-coated tablets.

Preparation Example 3

11.11 g of magnesium stearate was added to 1988.89 g of maleate of Compound A and the mixture was mixed for 30 minutes. The mixed powder was compression-molded by a roller compactor, and the solid obtained by molding was granulated. To 107.13 g of the resulting granulated powder were added 26.21 g of mannitol, 7.50 g of ethyl cellulose (ETHOCEL 100FP Premium, The Dow Chemical Company), 3.75 g of crystalline cellulose (CEOLUS KG-1000, Asahi Kasei Chemicals), 3.75 g of crospovidone (Kollidon CL-SF, BASF) and 0.75 g of croscarmellose sodium, and the mixture was mixed for 30 minutes. 0.90 g of magnesium stearate was added to the mixed powder and the mixture was mixed for 5 minutes. The mixed powder was tableted at a tableting pressure of about 7 kN using a pestle having a double rounded surface with a tablet diameter of 8.5 mm to obtain round uncoated tablets each weighing 315 mg. The uncoated tablets were coated with 9 mg of a coating agent per tablet, and then a small amount of carnauba wax was added thereto to give film-coated tablets.

The invention claimed is:

1. A method of reducing the amount of amyloid β protein in the brain, comprising administering 1-(3-(2-(1-Benzothiophen-5-yl)ethoxy)propyl)azetidin-3-ol or a salt thereof to a patient, wherein the amount of amyloid β protein in cerebrospinal fluid is increased by the administration of 1-3(2-1-Benzothiophen-5-yl)ethoxy)propyl)azetidine-3-ol or a salt thereof and the amount of amyloid β protein in the brain is reduced; and
   the patient is a patient who received prevention or therapy by administration of an acetylcholinesterase inhibitor for at least 4 months prior to administration of 1-(3-(2-(1-Benzothiophen-5-yl)ethoxy)propyl)azetidin-3-ol or a salt thereof.

2. The method of reducing the amount of amyloid β protein according to claim 1, wherein 1-(3-(2-(1-Benzothiophen-5-yl)ethoxy)propyl)azetidin-3-ol or a salt thereof is orally administered once a day in a dose of 100 mg to 400 mg in terms of 1-(3-(2-(1-Benzothiophen-5-yl)ethoxy)propyl)azetidin-3-ol per administration.

3. The method of reducing the amount of amyloid β protein according to claim 1, wherein 1-(3-(2-(1-Benzothiophen-5-yl)ethoxy)propyl)azetidin-3-ol or a salt thereof is orally administered once a day in a dose of 160 mg or 320 mg in terms of 1-(3-(2-(1-Benzothiophen-5-yl)ethoxy)propyl)azetidin-3-ol per administration.

4. The method of reducing the amount of amyloid β protein according to claim 1, wherein the method is for administration to a patient with a disease in which the amount of amyloid β protein in the brain is increased.

5. The method of reducing the amount of amyloid β protein according to claim 1, wherein the method is for administration to a patient with Alzheimer's disease, Probable Alzheimer's disease, Possible Alzheimer's disease, Preclinical Alzheimer's disease, Prodromal Alzheimer's disease, mild cognitive impairment due to Alzheimer's disease (MCI due to AD) or mild cognitive impairment.

6. The method of reducing the amount of amyloid β protein according to claim 1, wherein the method is for administration to a patient with Alzheimer's disease, mild cognitive impairment due to Alzheimer's disease (MCI due to AD) or mild cognitive impairment.

* * * * *